(12) United States Patent
Kuriger et al.

(10) Patent No.: US 12,357,789 B2
(45) Date of Patent: Jul. 15, 2025

(54) HUMIDIFICATION SYSTEM

(71) Applicant: Fisher & Paykel Healthcare Limited, Auckland (NZ)

(72) Inventors: Donald Roy Kuriger, Auckland (NZ); Johannes Nicolaas Bothma, Auckland (NZ); Igor Olegovich Yatsevich, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/309,988

(22) Filed: May 1, 2023

(65) Prior Publication Data
US 2023/0355914 A1    Nov. 9, 2023

Related U.S. Application Data

(63) Continuation of application No. 17/446,277, filed on Aug. 27, 2021, now Pat. No. 11,672,941, which is a
(Continued)

(51) Int. Cl.
*A61M 16/16* (2006.01)
*A61M 11/04* (2006.01)
(Continued)

(52) U.S. Cl.
CPC ........ *A61M 16/161* (2014.02); *A61M 11/042* (2014.02); *A61M 16/0833* (2014.02);
(Continued)

(58) Field of Classification Search
CPC ........ A61M 16/146; A61M 16/16–168; A61M 16/203; A61M 16/204; A61M 16/0833;
(Continued)

(56) References Cited

U.S. PATENT DOCUMENTS 1,678,625 A * 7/1928 Wallace ................ A61M 16/10
204/266
2,893,381 A   7/1959 Donald
(Continued)

FOREIGN PATENT DOCUMENTS

AU    2008202098    2/2009
CN    1489521    4/2004
(Continued)

OTHER PUBLICATIONS

"Fisher & Paykel Operating Manual: Heated Respiratory Humidifier MR410, Part No. 185040653, Revision E", Fisher & Paykel Healthcare, Mar. 1998, pp. 1-19 [Retrieved from the internet Dec. 11, 2015] <URL: http://www.medirents.net/Uploads/Modules/6eb4e7fa-a51e-4a5f-a7d8-9c6e4d3eef26.pdf>.
(Continued)

*Primary Examiner* — Valerie L Woodward
(74) *Attorney, Agent, or Firm* — VIA LLP

(57) ABSTRACT

A humidification system has a humidification source and a main gases flow path. The main gases flow path has a low pressure region and a high pressure region. In some embodiments, each of the low pressure region and the high pressure region has an aperture. The pressure difference between the apertures promotes a gases flow between the main gases flow path and the humidification source, and results in humidifying the gases in the main gases flow path.

27 Claims, 12 Drawing Sheets

Related U.S. Application Data continuation of application No. 16/060,119, filed as application No. PCT/IB2016/057285 on Dec. 2, 2016, now Pat. No. 11,135,395.

(60) Provisional application No. 62/266,123, filed on Dec. 11, 2015.

(51) Int. Cl.
*A61M 16/08* (2006.01)
*A61M 16/10* (2006.01)
*A61M 16/12* (2006.01)

(52) U.S. Cl.
CPC ........ *A61M 16/107* (2014.02); *A61M 16/127* (2014.02); *A61M 16/16* (2013.01); *A61M 2205/21* (2013.01); *A61M 2206/16* (2013.01)

(58) Field of Classification Search
CPC ........ A61M 16/0866; A61M 11/06–08; A61M 11/042; B01F 5/0413
See application file for complete search history.

(56) References Cited

U.S. PATENT DOCUMENTS

| | | | |
|---|---|---|---|
| 3,123,071 A | 3/1964 | Felts | |
| 3,221,737 A * | 12/1965 | Felts | A61M 16/147 128/203.25 |
| 3,451,409 A | 6/1969 | Roche | |
| 3,739,767 A | 6/1973 | Peters | |
| 3,842,828 A | 10/1974 | Bird | |
| 3,913,843 A | 10/1975 | Cambio | |
| 4,014,382 A | 3/1977 | Health | |
| 4,036,919 A | 7/1977 | Komendowski et al. | |
| 4,225,542 A | 9/1980 | Wall et al. | |
| 4,417,573 A | 11/1983 | De Vries | |
| 4,634,560 A * | 1/1987 | Eckert | B01F 25/312 261/78.2 |
| 4,773,448 A | 9/1988 | Francis | |
| 5,031,612 A | 7/1991 | Clementi | |
| 5,373,341 A | 12/1994 | Sangregory | |
| 5,373,841 A * | 12/1994 | Kyllonen | A61M 16/16 128/203.18 |
| 5,598,837 A | 2/1997 | Sirianne, Jr. et al. | |
| 5,632,270 A | 5/1997 | O'Mahony et al. | |
| 6,102,037 A | 8/2000 | Koch | |
| 6,230,666 B1 * | 5/2001 | Wallin | A61M 16/147 122/4 R |
| 6,531,206 B2 | 3/2003 | Johnston et al. | |
| 7,146,979 B2 | 12/2006 | Seakins et al. | |
| 7,509,957 B2 | 3/2009 | Duquette et al. | |
| 8,550,075 B2 | 10/2013 | Virr | |
| 9,132,250 B2 | 9/2015 | Allum et al. | |
| 9,242,064 B2 | 1/2016 | Rustad et al. | |
| 9,649,468 B2 | 5/2017 | Yatsevich et al. | |
| 10,130,784 B2 | 11/2018 | Yatsevich et al. | |
| 10,639,446 B2 | 5/2020 | Yatsevich et al. | |
| 11,058,843 B2 | 7/2021 | Yatsevich et al. | |
| 11,135,395 B2 | 10/2021 | Kuriger et al. | |
| 2004/0020487 A1 | 2/2004 | Koch et al. | |
| 2004/0118401 A1 | 6/2004 | Smith et al. | |
| 2004/0254524 A1 | 12/2004 | Spearman et al. | |
| 2005/0133615 A1 | 6/2005 | Gopalan | |
| 2006/0011198 A1 | 1/2006 | Matarasso | |
| 2006/0012057 A1 | 1/2006 | Anthony | |
| 2006/0070675 A1 | 4/2006 | Hsu | |
| 2007/0107879 A1 | 5/2007 | Drager | |
| 2007/0137646 A1 | 6/2007 | Weinstein et al. | |
| 2008/0105257 A1 | 5/2008 | Klasek | |
| 2009/0000620 A1 | 1/2009 | Virr | |
| 2010/0258114 A1 | 10/2010 | Cortez, Jr. et al. | |
| 2011/0023874 A1 | 2/2011 | Bath et al. | |
| 2011/0309157 A1 | 12/2011 | Yang et al. | |
| 2012/0125334 A1 | 5/2012 | Korneff et al. | |
| 2012/0307588 A1 | 12/2012 | Hanada et al. | |
| 2012/0318270 A1 * | 12/2012 | McAuley | A61M 16/0683 128/205.25 |
| 2015/0075529 A1 | 3/2015 | Romano | |
| 2016/0015915 A1 | 1/2016 | Paolo | |
| 2016/0058968 A1 | 3/2016 | Yatsevich et al. | |
| 2017/0216552 A1 | 8/2017 | Goff et al. | |
| 2017/0246416 A1 | 8/2017 | Yatsevich et al. | |
| 2018/0250490 A1 | 9/2018 | Burgess | |
| 2018/0361106 A1 | 12/2018 | Kuriger et al. | |
| 2019/0167938 A1 | 6/2019 | Yatsevich et al. | |
| 2020/0289778 A1 | 9/2020 | Yatsevich et al. | |
| 2021/0386960 A1 | 12/2021 | Yatsevich et al. | |
| 2022/0088341 A1 | 3/2022 | Yatsevich et al. | |

FOREIGN PATENT DOCUMENTS

| | | |
|---|---|---|
| DE | 10 2005 005349 | 6/2006 |
| DE | 10 2012 223445 | 6/2014 |
| EP | 1 586 345 | 10/2005 |
| FR | 2159732 A5 | 6/1973 |
| GB | 1 520 836 | 8/1978 |
| JP | 10-137339 | 5/1998 |
| WO | WO 83/03876 A1 | 11/1983 |
| WO | WO 1995/028193 | 10/1995 |
| WO | WO 1998/002199 | 1/1998 |
| WO | WO 1998/026826 | 6/1998 |
| WO | WO 2003/099367 | 12/2003 |
| WO | WO 2008/095245 | 8/2008 |
| WO | WO 2011/077250 | 6/2011 |
| WO | WO 2011/136665 | 11/2011 |
| WO | WO 2012/080923 | 6/2012 |
| WO | WO 2012/080941 | 6/2012 |
| WO | WO 2012/100291 | 8/2012 |
| WO | WO 2012/171072 | 12/2012 |
| WO | WO 2014/005191 | 1/2014 |
| WO | WO 2014/006574 | 1/2014 |
| WO | WO 2017/098386 | 6/2017 |

OTHER PUBLICATIONS

"MR850 Respiratory Humidifier Technical Manual, Revision J", Fisher & Paykel Healthcare, 2005, pp. 1-62 [Retrieved from the internet Dec. 11, 2015] <URL: http://www.nbngroup.com/manuals/machine/V-MR850TechManual.pdf>.

International Search Report for Application No. PCT/IB2016/057285; dated Feb. 7, 2017, 7 pages.

Australian Exam Report for Application No. 2016367428 dated Jan. 7, 2021, 5 pages.

* cited by examiner

HUMIDIFICATION SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Technical Field

The present disclosure generally relates to respiratory gas therapy. More particularly, the present disclosure relates to a system for the humidification of respiratory gases for use with respiratory gas therapy systems.

Description of Related Art

Respiratory disorders deal with the inability of a sufferer to effect a sufficient exchange of gases with the environment, leading to an imbalance of gases in the sufferer. These disorders can arise as a pathological consequence of an obstruction of the airway, insufficiency of the lungs in generating negative pressure, an irregularity in the nervous function of the brain stem, or some other physiological complication. Treatment of such disorders is diverse and depends on the particular respiratory disorder being targeted. In the first instance, a constriction of the airway, otherwise known as an obstructive apnea or a hypopnea (collectively referred to as obstructive sleep apnea or OSA), can occur when the muscles that normally keep the airway open in a patient relax during slumber to the extent that the airway is constrained or completely closed off, a phenomenon often manifesting itself in the form of snoring. When this occurs for a significant period of time, the patient's brain typically recognizes the threat of hypoxia and partially wakes the patient in order to open the airway so that normal breathing may resume. The patient may be unaware of these occurrences, which may occur as many as several hundred times per session of sleep. This partial awakening may significantly reduce the quality of the patient's sleep, over time potentially leading to a variety of symptoms, including chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that may reduce the frequency and/or duration of apneas, hypopneas, and/or flow limitations. This therapy may be delivered by using a positive airway pressure device (PAP device or blower) to propel a pressurized stream of air through a conduit to a patient through an interface or mask located on the face of the patient.

The stream of air may be heated to near body temperature. The stream of air may be humidified. The humidification may be performed by forcing the stream of air to travel through a respiratory humidifier containing water and a heater for heating the water. In such a system the heater encourages the evaporation of the water, which in turn partially or fully imbues the stream of air with moisture and/or heat. This moisture and/or heat may help to ameliorate discomfort that may arise from the use of un-humidified PAP therapy.

The entire gases flow may be passed through a humidifier in order to humidify the gases. For example the entire gases flow may pass through a humidifier chamber. The humidification chamber may comprise baffles or other features to create turbulence in the gases flow. There may be a substantial pressure drop across the chamber. The magnitude of the pressure drop across the chamber may vary and is dependent on the flow rate and the level of water in the chamber. The variability in the magnitude of the pressure drop may make it difficult to ensure a constant pressure is provided to a patient across all flow rates and humidification chamber water levels.

BRIEF SUMMARY

The systems, methods and devices described herein have innovative aspects, no single one of which is indispensable or solely responsible for their desirable attributes. Without limiting the scope of the claims, some of the advantageous features will now be summarized.

A humidification system may comprise a main gases flow path and a humidification source. The main gases flow path may comprise a gases inlet and a gases outlet. The main gases flow path may comprise regions of relatively high pressure and/or regions of relatively low pressure. Substantially at, or near, to these regions of relatively high and low pressure are inlet and/or outlet apertures. These apertures may provide for a pneumatic connection with a gases space in the humidification source.

The apertures generate gases flow either from the main gases flow path into the humidification source or, from the humidification source into the main gases flow path. The direction of the gases flow may be dependent on whether the aperture is near a region of the gases flow path that is of a relatively high pressure or a relatively low pressure. An aperture near an area of relatively high pressure generates a flow of gases out of the main gases flow path and is an outlet aperture. An aperture near an area of relatively low pressure generates a flow of gases into the main gases flow path and is an inlet aperture. In some embodiments the humidification source comprises a humidification chamber. The humidification chamber is configured to provide humidification to gases in a gases space of the humidification chamber. The apertures generate gases flow either from the main gases flow path into the humidification chamber or, from the humidification chamber into the main gases flow path.

The regions of relatively high and low pressure can be generated by a change in cross sectional area of the main gases flow path or, features in the main gases flow path. The main gases flow path may comprise a series of inlet and/or outlet apertures, which generate a secondary gases flow through the humidification chamber. The secondary gases flow may be flow from the main gases flow, through an outlet aperture(s), through the gases space of the humidification chamber and through an inlet aperture back into the gases flow path.

The direction of this secondary gases flow may be in substantially the same direction or an opposite direction to the gases flow. The direction of the secondary gases flow is dependent on the relative positions of the inlet and outlet apertures along the gases flow path. For example if the inlet aperture(s) is/are located prior to the outlet aperture(s), then the secondary gases flow will be in the substantially the same direction as the main gases flow. If the outlet aperture(s) is/are located prior to the inlet aperture(s) then the secondary gases flow will be in substantially the opposite direction to the main gases flow. If the secondary gases flow is in the opposite direction to the main gases flow the main gases flow may be recirculated, at least to an extent, through the humidification chamber.

In accordance with a first aspect of at least one embodiment disclosed herein, a humidification system comprises:
 a humidification source configured to humidify gases,
 a main gases flow path comprising a low pressure region, and a high pressure region,
 wherein the main gases flow path comprises an outlet aperture near the high pressure region, the outlet aperture pneumatically connected to the humidification source to allow a flow of gases from the main gases flow path into the humidification source, and
 wherein the main gases flow path comprises an inlet aperture near the low pressure region, the inlet aperture pneumatically connected to the humidification source to allow a flow of gases from the humidification source into the main gases flow path.

In some embodiments, the humidification source comprises a humidification chamber.

In some embodiments, the outlet aperture is located downstream to the inlet aperture along the main gases flow path.

In some embodiments, the outlet aperture is located upstream to the inlet aperture along the main gases flow path.

In some embodiments, the main gases flow path further comprises a neck portion, an inlet portion and an outlet portion, wherein the neck portion is of a smaller cross sectional area than the inlet and/or outlet portions.

In some embodiments, the outlet aperture is located near at least one of the inlet portion and/or the outlet portion.

In some embodiments, the humidification chamber is sealed to an external environment.

In some embodiments, the humidification chamber comprises a valve or an aperture configured to allow gas exchange with an external environment.

In some embodiments, the valve or the aperture is configured to only allow gases from the external environment into the humidification chamber.

In some embodiments, a flow of gases from the humidification source to the main gases flow path is between 0% and 40%, or between 10% and 30%, or is about 20% or is about 10% of a flow of gases through the main gases flow path.

In some embodiments, the humidification chamber further comprises a heater configured to heat the humidification chamber, wherein the heater is a heater plate.

In some embodiments, the cross sectional area of a part of the main gases flow path is variable.

In some embodiments, the cross sectional area of a part of the neck portion, inlet portion and/or outlet portion is variable.

In some embodiments, the main gases flow path comprises a valve, the valve configured to vary the flow rate of gases through the main gases flow path.

In some embodiments, the main gases flow path comprises a feature configured to change at least one of pressure, velocity, flow rate and a flow profile of the flow of gases through the main gases flow path.

In some embodiments, the feature is at least one of a baffle, diffuser, orifice plate, or texture on the surface of the main gases flow path.

In some embodiments, the feature is actuatable to vary at least one of pressure, velocity, flow rate and a flow profile of the flow of gases through the main gases flow path.

In accordance with a second aspect of at least one embodiment disclosed herein, a humidification system comprises:
 a main gases flow path,
 a humidification source,
 wherein the main gases flow path comprises a first portion and a second portion,
 wherein the first portion comprises a larger cross sectional area than the second portion so that with a flow of gases through the main gases flow path a high pressure region is generated in the first portion and a low pressure region is generated in the second portion, and
 an inlet aperture, the inlet aperture being positioned at or near the low pressure region to allow a gases flow from the humidification source to the main gases flow path.

In some embodiments, the gases flow through the main gases flow path from the first portion to the second portion.

In some embodiments, the gases flow through the main gases flow path from the second portion to the first portion.

In some embodiments, the main gases flow path further comprises a transition portion pneumatically connecting the first portion and the second portion.

In some embodiments, the inlet aperture is provided at the transition portion.

In some embodiments, the first portion tapers from a larger cross section to a smaller cross section at or adjacent to the second portion.

In some embodiments, the first portion is an inlet portion and the gases flow path further comprises an outlet portion, and wherein the second portion is a neck portion in between the inlet and outlet portions, the neck portion having a smaller cross sectional area than the inlet and outlet portions, and
 with a flow of gases through the main gases flow path a high pressure region is generated in the inlet and outlet portions and a low pressure region is generated in the neck portion.

In some embodiments, the outlet portion tapers from a larger cross section to a smaller cross section at or adjacent to the neck portion.

In some embodiments, the system further comprises an outlet aperture at or near the high pressure region to allow a flow of gases from the main gases flow path into the humidification source.

In some embodiments, the outlet aperture is adjacent to an inlet or an outlet of the main gases flow path.

In some embodiments, the outlet aperture is located downstream to the inlet aperture along the main gases flow path.

In some embodiments, the outlet aperture is located upstream to the inlet aperture along the main gases flow path.

In some embodiments, the humidification source comprises a valve or an aperture allowing gas exchange with an external environment.

In some embodiments, the valve or the aperture is configured to only allow gases from the external environment into the humidification chamber.

In some embodiments, the humidification source is sealed from an external environment but for a flow path through the source via the outlet aperture and the inlet aperture.

In some embodiments, a flow of gases from the humidification source to the main gases flow path is between 0% and 40%, or between 10% and 30%, or is about 20% or is about 10% of a flow of gases through the main gases flow path.

In some embodiments, the cross sectional area of a part of the main gases flow path is variable.

In some embodiments, the cross sectional area of a part of the neck portion, inlet portion and/or outlet portion is variable.

In some embodiments, the system further comprises a valve configured to vary the flow rate of gases through the main gases flow path.

In some embodiments, the main gases flow path comprises a feature configured to change at least one of pressure, velocity, flow rate and a flow profile of the flow of gases through the main gases flow path.

In some embodiments, the system comprises a feature between the humidification source and the main gases flow path, the feature configured to change at least one of pressure, velocity, flow rate and a flow profile of a flow of gases from the humidification source to the main gases flow path.

In some embodiments, the feature is at least one of a valve, baffle, diffuser, orifice plate, or texture on the surface of the main gases flow path or in contact with the flow of gases.

In some embodiments, the feature is actuatable to vary at least one of pressure, velocity, flow rate and a flow profile of the flow of gases through the main gases flow path In some embodiments, the humidification source comprises a humidification chamber.

In some embodiments, the humidification source further comprises a heater configured to heat the humidification chamber. In some embodiments the heater is a heater plate.

In some embodiments, the main gases flow path is formed in a lid component of the humidification chamber or a tubular component passing through a gases space of the humidification chamber.

In some embodiments, the system further comprises a connector, the connector comprising the main gases flow path and a humidification inlet portion to connect to a hose or conduit to the humidification source, the humidification inlet portion in communication with the inlet aperture.

In some embodiments, the connector is a T or Y connector.

In some embodiments, the inlet aperture comprises an annular cavity extending at least part way around the main gases flow path.

In some embodiments, the annular cavity comprises a toroid cavity with a half cylinder cross section opening into the main gases flow path towards an inlet end of the main gases flow path In some embodiments, the system further comprises a structure adapted to cause gases flow from the main gases flow path to swirl.

In some embodiments, the structure comprises one or more vanes or baffles that interfere with the gases flow to cause the flow to swirl.

In some embodiments, the structure is downstream to the inlet aperture or at or adjacent to an outlet of the main gases flow path.

In accordance with a third aspect of at least one embodiment disclosed herein, a humidification system comprises:
a main gases flow path,
a secondary gases flow path (or a shunt path),
a humidification chamber,
wherein the secondary flow path extends from the main gases flow path, into the humidification chamber and back into the main gases flow path.

In some embodiments, the secondary flow path extends from the main gases flow into the humidification chamber before the secondary flow path enters the main gases flow path.

In some embodiments, the secondary flow path extends from the main gases flow into the humidification chamber after the secondary flow path enters the main gases flow path.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

DETAILED DESCRIPTION

Figure 1:
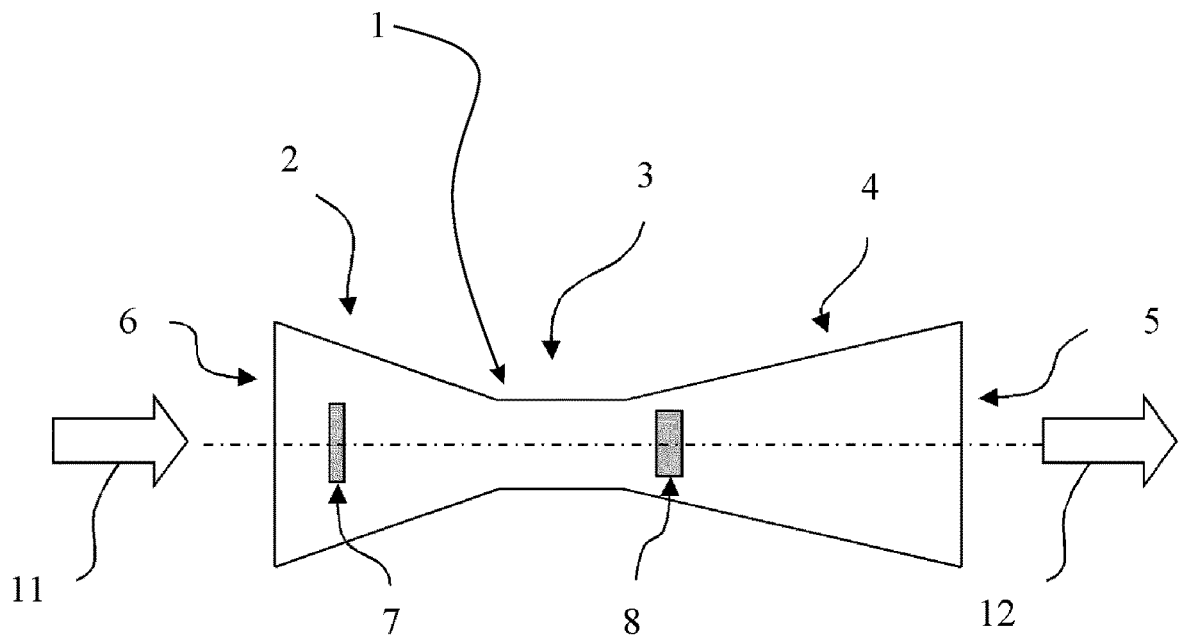
FIG. 1 shows a top view of a cross section of a main gases flow path configured to generate regions of low and high pressure.

A humidification system may comprise a main gases flow path and a humidification source. The main gases flow path may comprise a gases inlet and a gases outlet. The main gases flow path may comprise regions of relatively high pressure and/or regions of relatively low pressure. The regions of relatively high pressure and/or regions of relatively low pressure can be generated by at least one of: a change in cross sectional area of the flow path, a change in the surface of the flow path, a change in features of the flow path itself (for example, baffles or fins). The change in pressure may be at least partially recoverable or unrecoverable. If the pressure change is caused by, for example, a change in the flow cross-sectional area, the change may be reversible in that reversing the change in area will reverse the change in pressure. One such example of a way to change pressure in a recoverable manner is by using a venturi.

Generally, a gases flow may be generated from an area of higher pressure to an area of lower pressure. The gases flow path may comprise at least one aperture substantially at or near the regions of high or low pressure. A gases flow may be generated from the at least one aperture; its flow direction being dependent on whether the at least one aperture is substantially near a region of high or low pressure of the gases flow path. Where the at least one aperture is near a high pressure region the flow direction of gases through the aperture will be from or out of the main gases flow path. Where the at least one aperture is near a low pressure region the flow direction of gases through the aperture will be into the main gases flow path. The at least one aperture may provide a pneumatic connection between the gases flow path and the humidification source allowing a gases flow from the main gases flow path to the humidification source, and/or from the humidification source to the gases flow path.

In some embodiments the main gases flow path may comprise features to change the flow characteristics of the gases flow. The features may comprise at least one of surface features on the surface of the gases flow path, baffles, an orifice plate, or a diffuser. In some embodiments these features may influence the pressure, velocity, or flow profile (in terms of which parts of the flow are turbulent or laminar). In some embodiments the features are actuatable such that their effect on the gases flow varies. The features may be actuated to change at least one of: their angle of attack relative to the gases flow path, or their geometric profile or area.

When the terms 'high pressure' or 'relatively high pressure' are used they are to be interpreted as referring to a higher pressure relative to at least one of: the average pressure of the system, the pressure in the humidification source, or atmospheric pressure.

When the terms 'low pressure' or 'relatively lower pressure' are used they are to be interpreted as referring to a lower pressure relative to at least one of: the average pressure of the system, the pressure in the humidification source, or atmospheric pressure.

The humidification source is configured to provide humidification to gases. In some embodiments the humidification source comprises a humidification chamber. In some embodiments the humidification chamber adds water vapour to gases in the chamber. The humidification chamber may comprise a heater configured to warm the liquid in the humidification chamber. In some embodiments the heater comprises a heater plate. In some embodiments the heater is provided within the chamber, or external to the chamber to heat the contents of the chamber via a side or bottom of the chamber.

Figure 2:
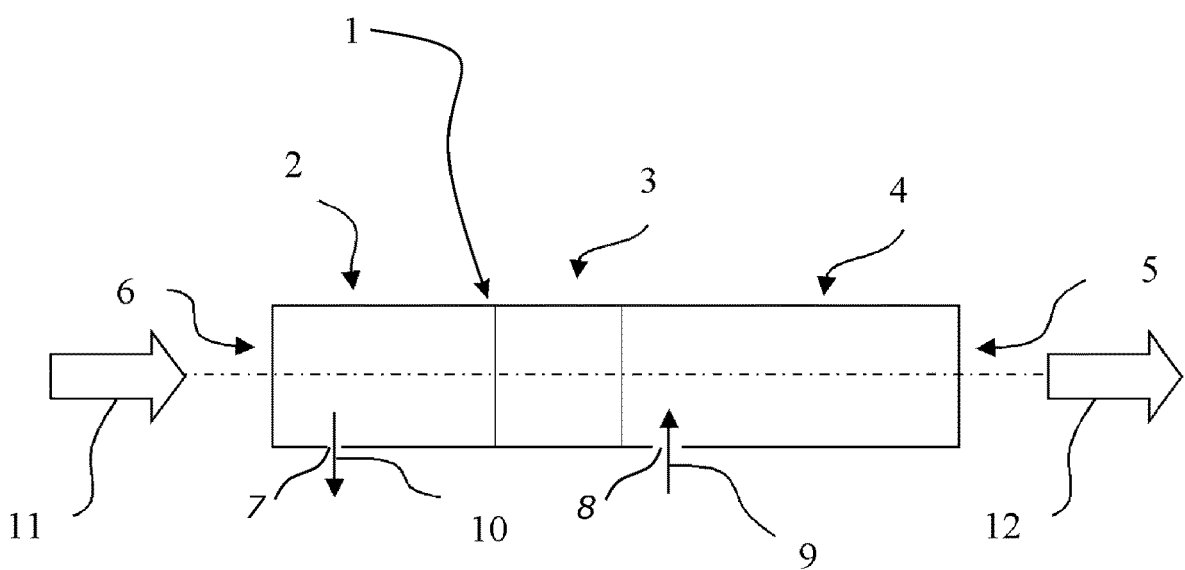
FIG. 2 shows a side view of a cross section of a main gases flow path configured to generate regions of low and high pressure.

FIGS. 1 and 2 show a top and side view, respectively, of a main gases flow path 1 configured to generate regions of low and high pressure. The main gases flow path 1 comprises an inlet portion 2, a neck 3 and an outlet portion 4. The main gases flow is indicated by the arrows 11, 12. Gases flow enters the main gases flow path 1 at the gases inlet 6, passes through the inlet portion 2, neck portion 3 and outlet portion 4 and exits the main gases flow path 1 at the gases outlet 5. The main gases flow path comprises an outlet aperture 7 and an inlet aperture 8. In some embodiments the outlet aperture 7 is located generally in the inlet portion 2 of the main gases flow path 1. In some embodiments the inlet aperture 8 is located generally in the neck portion 3, the outlet portion 4 or a combination thereof. In some embodiments there may be multiple inlet and/or outlet apertures located in at least one of the inlet portion 2, the neck portion 3 and/or the outlet portion. In some embodiments there is no outlet aperture; instead the humidification chamber 13 is connected to atmosphere. In these embodiments there is only an inlet aperture 8 which acts to draw in gases from the humidification chamber 13. In some embodiments the humidification chamber is sealed airtight. In some embodiments the humidification chamber comprises a valve to allow for gas exchange with the external environment. The humidification chamber may comprise a heater plate 15 configured to transfer energy to a liquid 14 (for example water).

The relative pressure and velocity of the gases varies along the flow path 11, 12 and is related to the cross sectional area of the flow path at a particular point. The relationship between static pressure and velocity at any point can be determined by a simplified version of the Bernoulli equation (assuming there is no change in height of the flow path.)

$$\frac{1}{2}\rho v^2 + p = \text{Constant} \qquad \text{(Equation 1)}$$

Where:
v=the velocity of the gas
p=the static pressure at a particular point
ρ=the density of the gas This equation illustrates that an increase in velocity will lead to a decrease in pressure and vice versa. Therefore for portions of the main gases flow path which have lower velocities relative to other parts of the main gases flow path, these portions will have a higher relative static pressure.

The relationship between volumetric flow rate, velocity and area can be described by the equation below:

$$Q = vA \qquad \text{(Equation 2)}$$

Where:
Q=Volumetric flow rate
v=the velocity of the gas
A=Cross sectional area

This equation illustrates that if there is constant volumetric flow a decrease in cross sectional area will lead to an increase in velocity and vice versa.

The inlet portion 2 and the outlet portion 4 may have larger cross sectional areas than the neck portion 3. The cross sectional area of the inlet portion 2 tapers from a larger cross section at the gases inlet 6 to a smaller cross section where the inlet portion 2 transitions to the neck portion 3. In some embodiments, the neck portion has a substantially constant cross section for its entire length. In some embodiments the neck portion may be tapered. The taper may increase or decrease the cross sectional area along the gases flow path. The cross sectional area of the outlet portion 4 tapers from the smaller cross section where the neck portion 3 transitions to the outlet portion 4, to a larger cross section at the gases outlet 5. The tapers described above may be at a constant pitch or the pitch may vary along the taper.

In some embodiments any of the inlet, neck or outlet portions 2,3,4 may comprise a combination of smaller sub portions of which each may decrease, increase or remain constant in cross sectional area by altering the shapes and/or dimensions. In some embodiments, inlet portion and the outlet portion have substantially the same cross sectional area. In some embodiments, the inlet portion may have a larger cross sectional area than the outlet portion. In other embodiments, the outlet portion may have a larger cross sectional area than the inlet portion.

Applying equation 2 to the main gases flow path 1 of FIG. 1, the gases passing through the inlet portion 2 and the outlet portion 4 have a lower velocity relative to the velocity of the gases passing though the neck portion 3. Further, then applying equation 1 the gases passing through the inlet portion 2 and the outlet portion 4 have a higher pressure relative to the gases passing through the neck portion.

Figure 3:
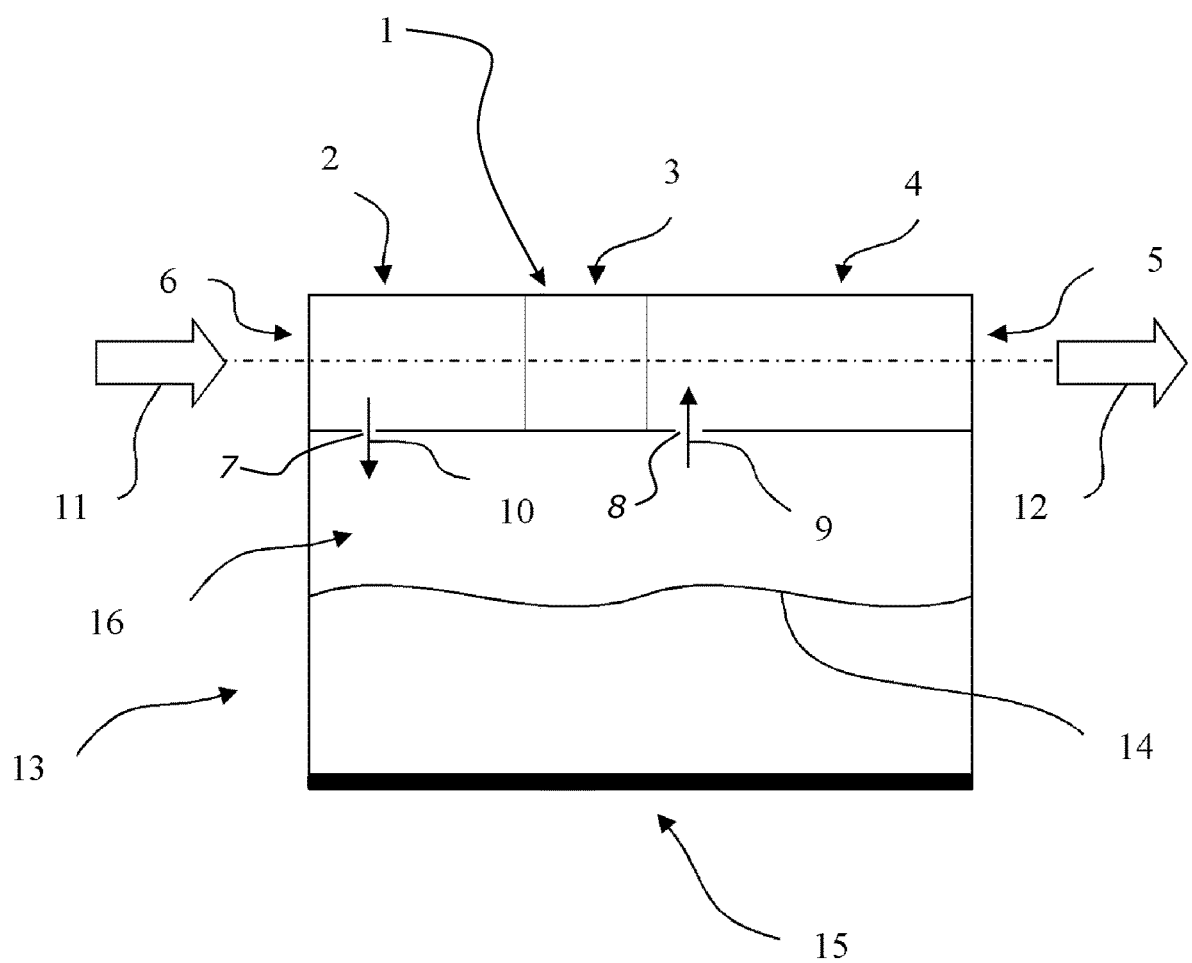
FIG. 3 shows a side view of a cross section of a humidification system comprising the main gases flow path of FIGS. 1 and 2.

FIG. 3 shows a cross sectional side view of a main gases flow path 1 and a humidification chamber 13. The outlet aperture 7 and inlet aperture 8 allow for a pneumatic connection between the main gases flow 11, 12 and a gases space of the humidification chamber 13. In some embodiments, the outlet aperture 7 and inlet aperture 8 act to provide a shunt (e.g. parallel) or secondary flow path to divert a portion of the gases flow 11, 12 in the main gases flow path from the main gases flow path through the humidification chamber 13 and back into the main gases flow path. As the shunted or secondary flow path gas passes through the humidification chamber 13, it is humidified. Once the humidified gas rejoins the main gases flow path 1, it mixes with the main gases flow 11, 12. The mixture comprises the warmed and humidified gas from the shunt or secondary path and the gas from the main gases flow path 1.

The pressure inside the main gases flow path 1 near the outlet aperture 7 is greater than the pressure inside the humidification source 13 and inside the main gases flow path 1 near the inlet aperture 8. The pressure in the humidification source 13 is greater than the pressure inside the main gases flow path 1 near the inlet aperture 8. This pressure gradient drives a flow of gas from the main gases flow path 1 into the humidification chamber 13 and then back into the main gases flow path 1. The higher pressure area inside the main gases flow path 1 near the outlet aperture 7 drives an outlet gases flow 10 from the main gases flow path 1 into the humidification chamber 13. The low pressure area inside the main gases flow path near the inlet aperture 8 drives an inlet gases flow 9 from the humidification chamber 13 into the main gases flow path 1.

In some embodiments, the flow rate of the shunted of secondary flow path gas (the inlet and outlet gases flows) is substantially smaller than that of the main gases flow. In some embodiments, the flow rate of the shunted or secondary flow path gas is between 0% and 40% of the main gases flow. In some embodiments, the flow rate of the shunted or secondary flow path gas is between 10% and 30% of the main gases flow. In some embodiments, the flow rate of the shunted or secondary flow path gas is 20% or 10% of the main gases flow.

Figure 4:
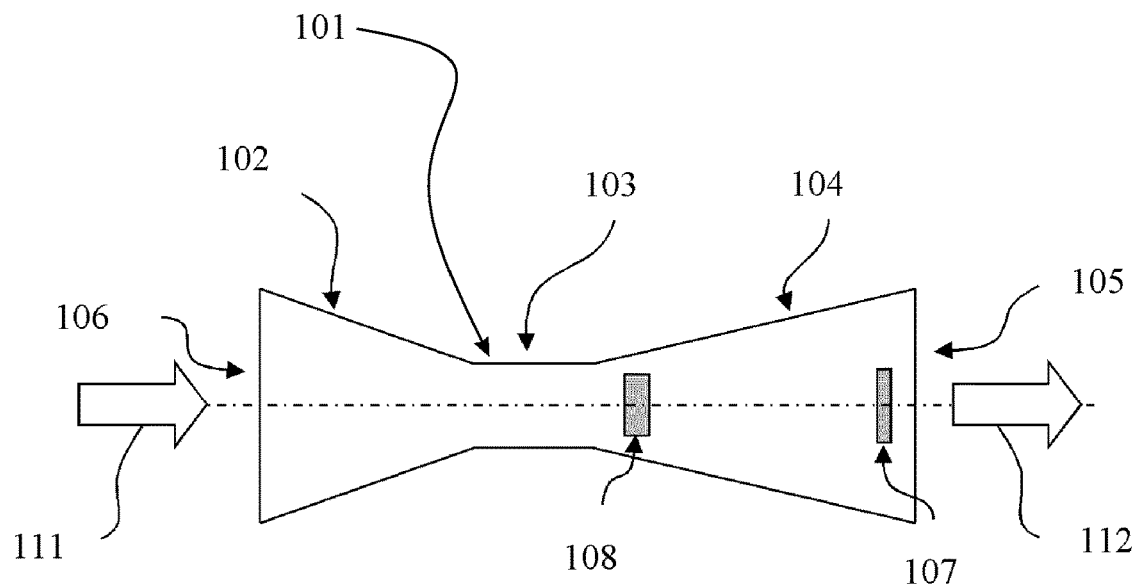
FIG. 4 shows a top view of a cross section of a main gases flow path configured to FIG. 5 shows a side view of a cross section of a main gases flow path configured to generate regions of low and high pressure.
Figure 5:
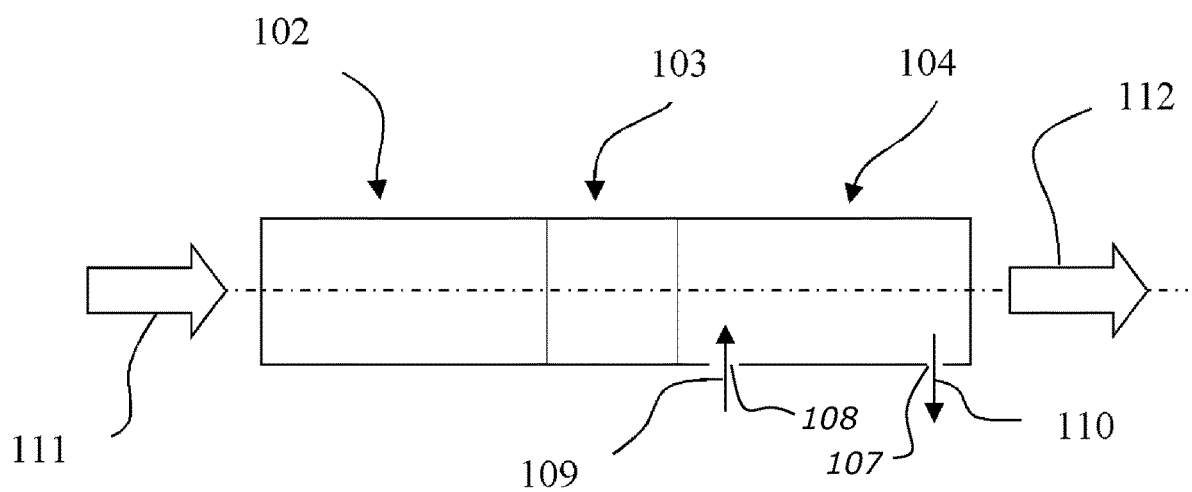
Figure 6:
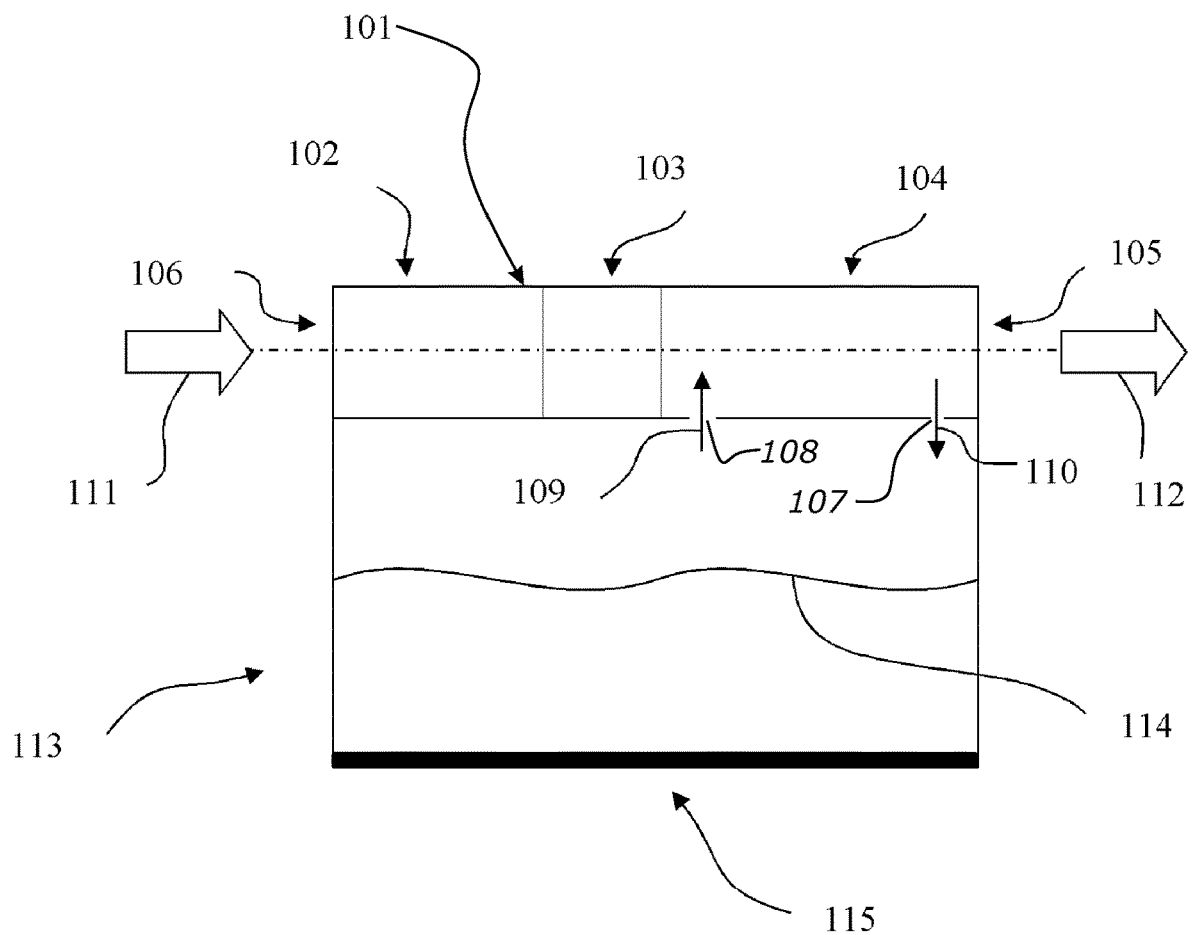
FIG. 6 shows a side view of a cross section of a main gases flow path configured to generate regions of low and high pressure.

FIGS. 4 and 5 show top and side views, respectively, of an embodiment of a main gases flow path 101. FIG. 6 shows the main gases flow path 101 as part of a humidification system. The main gases flow path 101 may be a venturi and may comprise an inlet portion 102, a neck portion 103, and an outlet portion 104. Gases flow into the gases inlet 106 along the gases flow path 111, 112 and out the gases outlet 105. The main gases flow path 101 also comprises an inlet aperture 108 and an outlet aperture 107. In some embodiments, the outlet aperture 107 is located near the outlet portion 104 and optionally near the gases outlet 105. The inlet aperture 108 is located near the neck portion 103.

The humidification system may comprise a main gases flow path 101 and the humidification source may comprise a humidification chamber 113. The humidification chamber may comprise a heater plate 115 configured to transfer energy to a liquid 114 (for example, water). Due to the pressure difference between the inlet aperture 108 and outlet aperture 107, an inlet gases flow 109 and an outlet gases flow 110 will be generated. Water vapour is added to the gases flow 110 as it passes though the humidification chamber. The further humidified gas then flows through the inlet aperture 110 and back into the main gases flow path 101.

In some embodiments, such as that shown in FIGS. 4 and 5, the inlet aperture 108 is located before the outlet aperture 107 in the main gases flow path 101. In these embodiments at least part of the gas in the main gases flow path 101 may be recirculated through the humidification chamber 113 multiple times.

Figure 7:
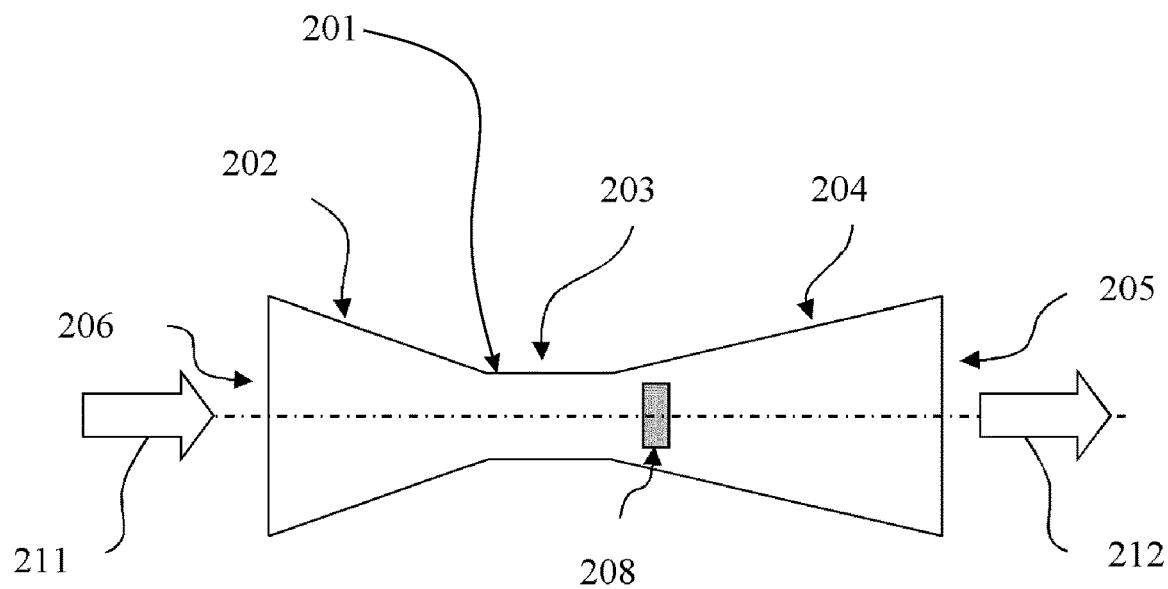
FIG. 7 shows a side view of a cross section of a main gases flow path configured to generate regions of low and high pressure.
Figure 8:
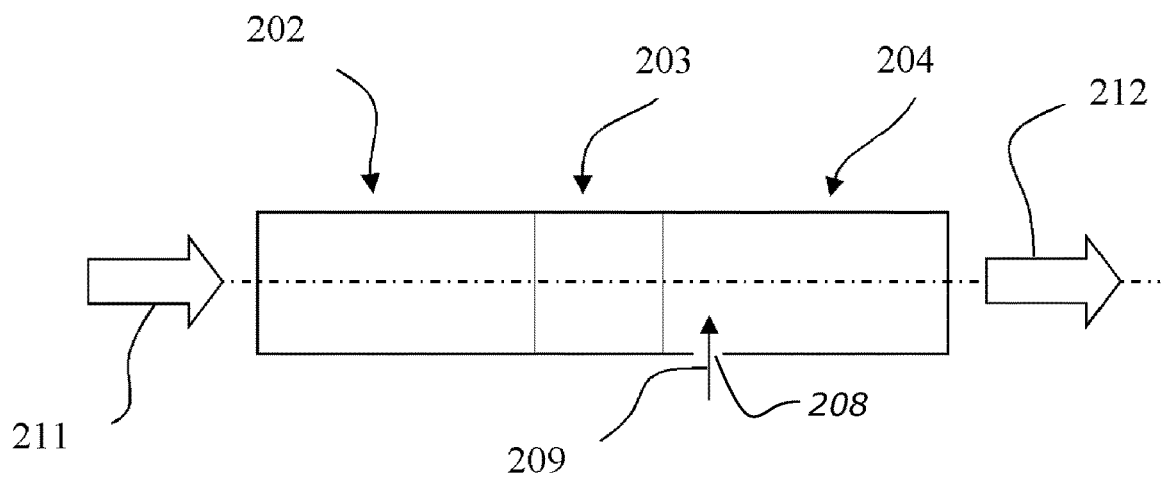
FIG. 8 shows a side view of a cross section of a humidification system comprising the main gases flow path of FIGS. 6 and 7.
Figure 9:
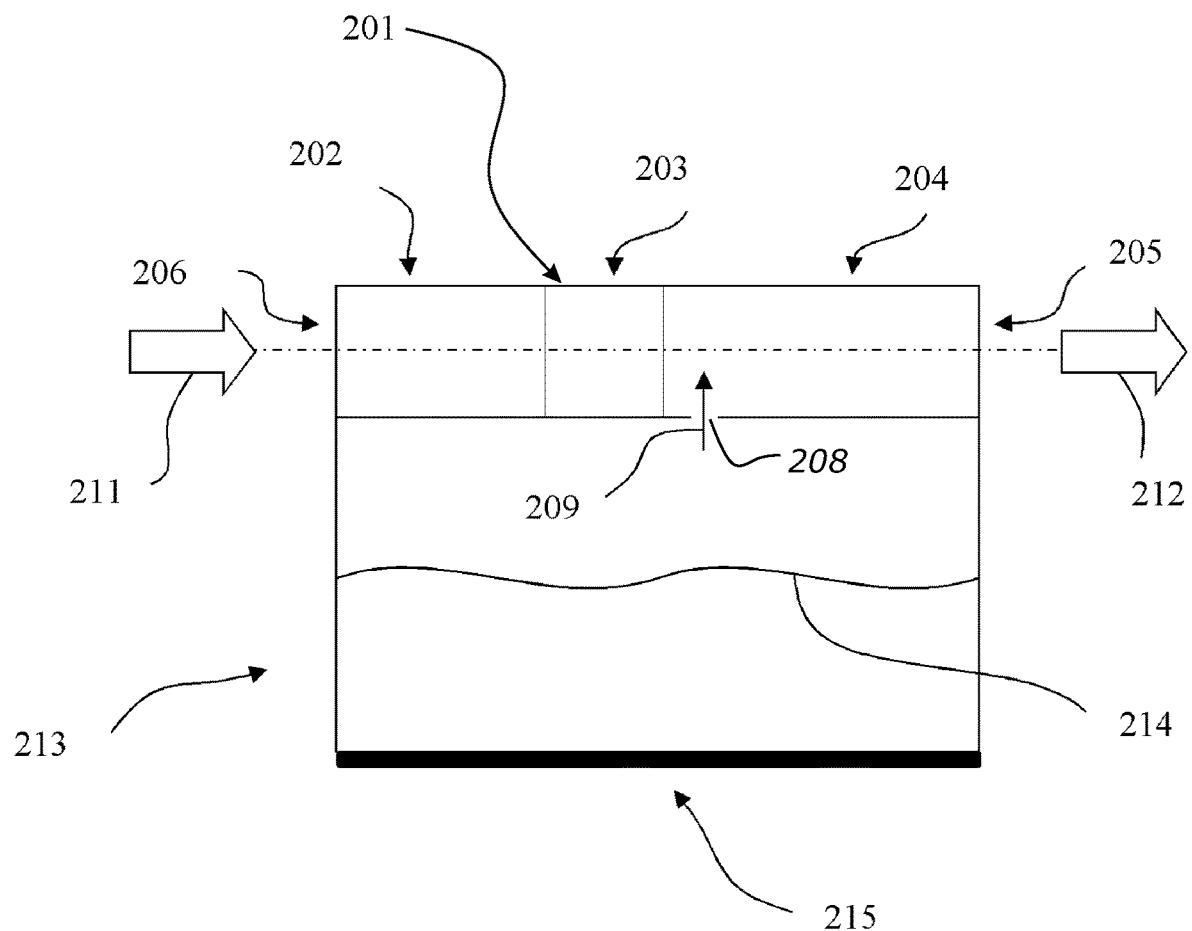
FIG. 9 shows a top view of a cross section of a main gases flow path configured to generate regions of low and high pressure.

FIGS. 7 and 8 show side views of a main gases flow path 201 and FIG. 9 shows the main gases flow path 201 as part of a humidification system. In some embodiments, the main gases flow path 201 comprises an inlet aperture 208 located near the neck portion 203, and is without an outlet aperture. In these embodiments, the low pressure area near the inlet aperture 208 acts to generate a flow of gases 209 from the humidification chamber 213 into the main gases flow path 201. In some embodiments, the humidification chamber 213 is not sealed to the external environment. This allows for gases to flow from the external environment into the humidification chamber 213 and replace the gas that has been transferred to the main gases flow 211, 212. Therefore no outlet aperture is necessary since flow enters the chamber from the atmosphere and not via the main gases flow path. In some embodiments the humidification source comprises an inlet, allowing a flow of gases to enter the humidification source, the inlet separate from the main gases flow path so that gases enter the humidification source before entering the main gases flow path via the inlet aperture 208.

In some embodiments, the humidification chamber comprises a valve configured to allow for a gas exchange between the external environment and the humidification chamber 213. In some embodiments, the valve is a one way valve that only allows flow of gases into the humidification chamber 213.

In some embodiments, the pressure at a region of the gases flow path may be varied. In some embodiments, the pressure near at least the neck, inlet or outlet region(s) is varied. In some embodiments, the orientation of features in the flow path is changed. For example, the angle of a baffle or other feature to the direction of the flow of gases along the main flow path may be varied to create an area of low or high pressure. In some embodiments, the cross sectional area of the flow path can be varied. The cross sectional area may be varied by, for example, a valve or by compression or deformation of the flow path.

In some embodiments at least part of the main gases flow path may be made of a malleable material such as a plastic, for example, a rubber or a polymer. Part of the main gases flow path may be deformed under an externally applied force (e.g. by a screw or other mechanism) such that a cross sectional area of the part of the main gases flow path may be varied. By varying the cross section of the main gases flow path the proportion of gases flow from the humidification source entering the main gases flow path may be controlled.

In the above described embodiments illustrated in FIGS. 1 to 9, the inlet portion 2, 102, 202 is a first portion, and the neck portion 3, 103, 203 is a second portion. The first portion 2, 102, 103 comprises a larger cross sectional area than the second portion 3, 103, 203 so that with a flow of gases 11, 12, 111, 112, 211, 212 through the main gases flow path 1, 101, 201 a high pressure region is generated in the first portion 2, 102, 103 and a low pressure region is generated in the second portion 3, 103, 203. The inlet aperture 8, 108, 208 is located near to (e.g. close to or in) the second portion 3, 103, 203 so that the inlet aperture is near to or in the low pressure region. The low pressure region has a pressure less than a pressure of the humidification source, such that a pressure gradient is created between the humidification source and the low pressure region, causing a flow from the humidification source to the main gases flow path. In the embodiment of FIGS. 7 to 9, the inlet aperture is illustrated as being near to and slightly downstream of the neck or second portion of the main gases flow path. Alternatively, the inlet aperture may be in or slightly upstream of the neck or second portion.

Figure 10:
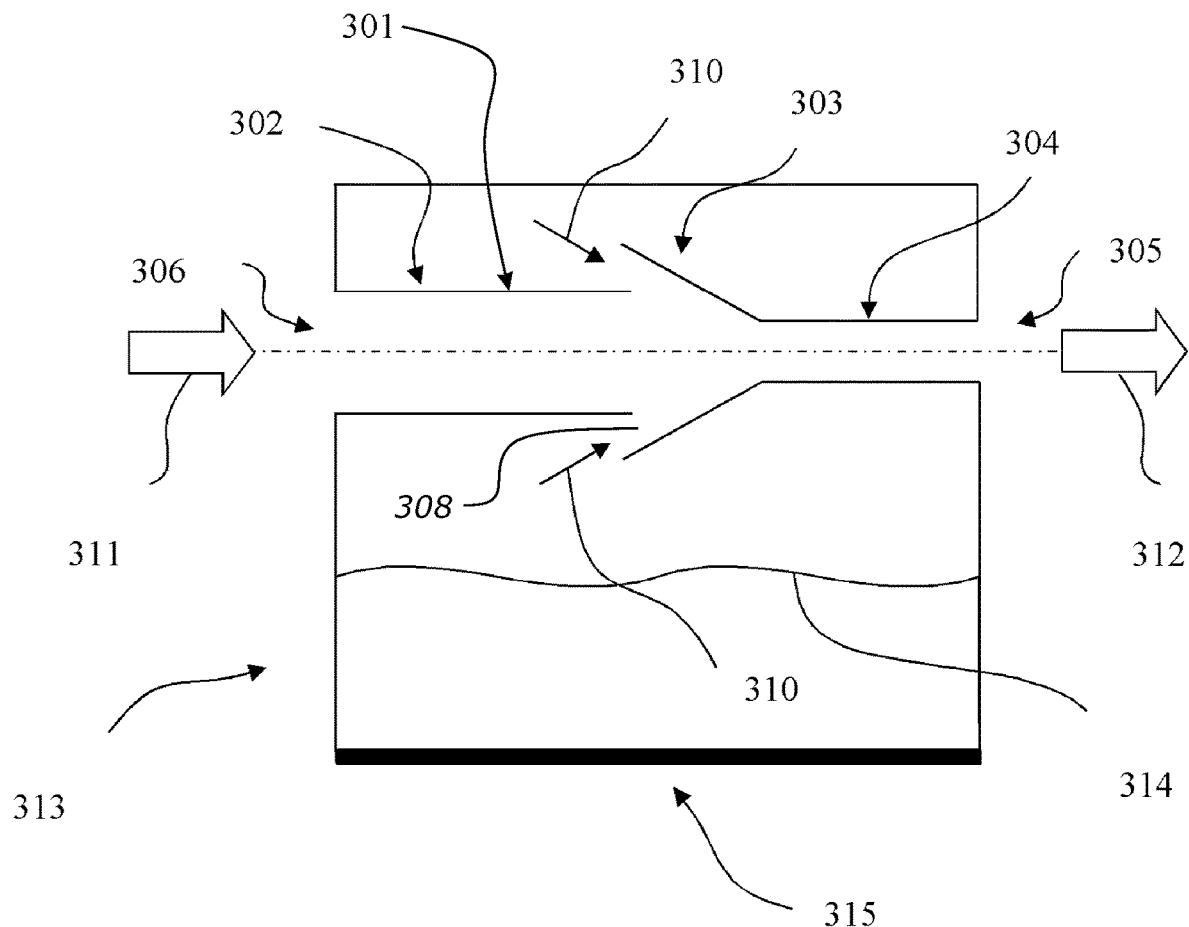
FIG. 10 shows a side view of a cross section of a humidification system comprising a gases flow path configured to generate regions of low and high pressure.

FIG. 10 shows an embodiment comprising a humidification chamber 313 and a main gases flow path 301. The main gases flow path 301 comprises features configured to generate a gases flow 310 from the humidification chamber 313 into the main gases flow 311, 312. The main gases flow path 301 comprises a gases inlet 306, a first portion 302, a second portion 304, a third portion 303, and a gases outlet 305. Gases flow into the gases inlet 306, pass through the first portion to the second portion via the third portion and out the gases outlet 305.

The cross sectional area of the first portion 302 is greater than that of the second portion 304. Therefore, the velocity of the main gases flow 311, 312 is greater in the second portion 304 than it is in the first portion 302. This means the pressure in the second portion 304 is lower than the pressure in the first portion 302. This lower pressure region generates a gases flow 310 from the humidification chamber 313 into the main gases flow path 301. The gases flow 310 may contain water vapour provided to the gases flow 310 in the humidification chamber 313. The third portion 303 is of a funnel type shape and acts to transition the main gases flow 311, 312 from the first portion 302 to the second portion 303 and to provide a path for the gases flow 310 from the humidification chamber. The third portion 303 may be described as a transition portion, transitioning from the first portion 302 to the second portion 304, e.g. by tapering from a larger cross section to the smaller cross section of the second portion. An inlet aperture 308 may be provided at the transition portion, for the gases to pass from the chamber 313 to the main gases path 301. The inlet may be formed as an annular opening extending around the first portion 302 of the main gases flow path. The chamber may comprise an inlet (not shown in FIG. 10), allowing a flow of gases to enter the humidification chamber, the inlet separate from the main gases flow path so that gases enter the humidification source before entering the main gases flow path via the inlet aperture 308.

In some embodiments, the third portion 303 may be integrally formed with at least one of the first 302 and second 304 portions and the gases flow 310 may be generated by an aperture located in either the second portion 304 or the third portion 303. In some embodiments, the humidification chamber may be sealed and an aperture may be present in the first portion 302 to generate a flow of gases from the main gases flow path 301 into the humidification chamber 313.

In some embodiments, the inlet apertures of any of the humidification systems described above may comprise a valve, snorkel arrangement, membrane, filter, or the like configured to reduce the likelihood of water ingress into the gases flow path. The valve, membrane, or filter may be configured to reduce the likelihood of water ingress into the gases flow path but to allow gases therethrough. The snorkel arrangement may comprise a tortuous pathway that, in the case of where the humidification system is tilted or inverted, reduces the likelihood of flow into the gases flow path.

Figure 11:
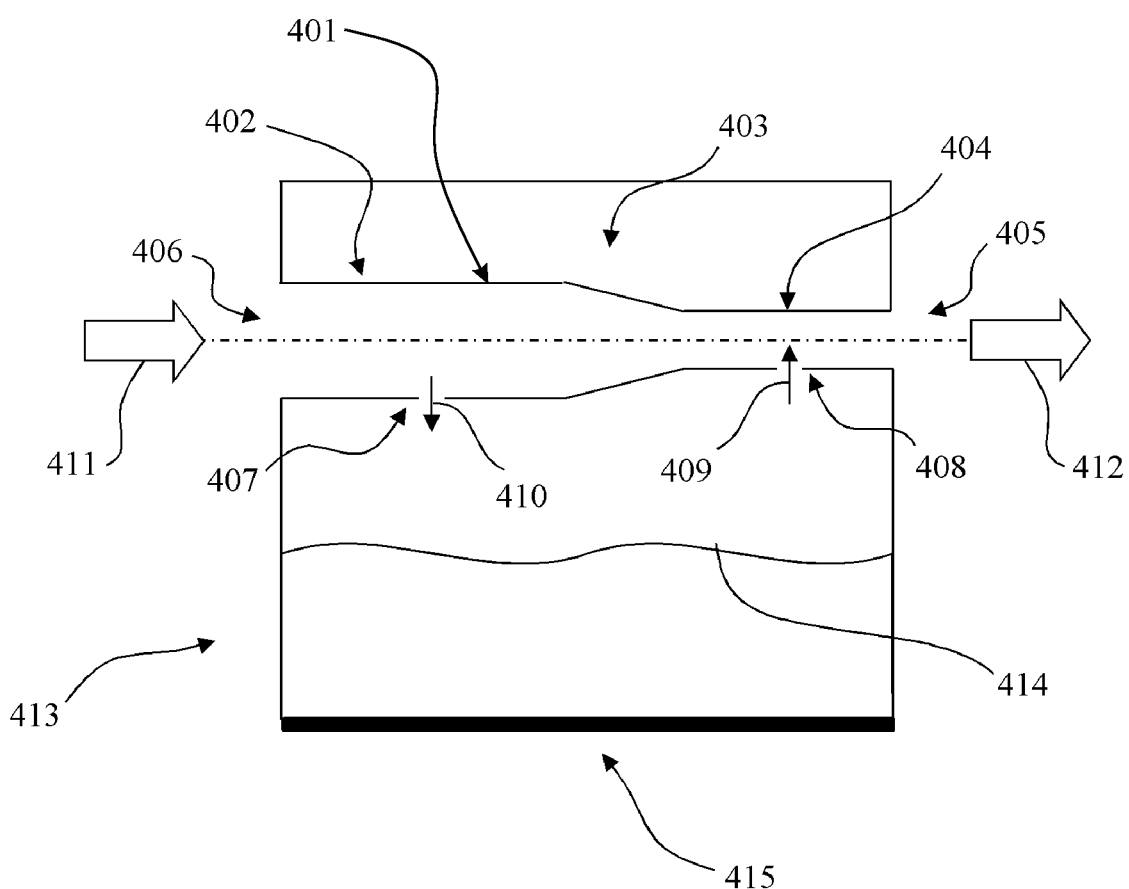
FIG. 11 shows a side view of a cross section of a humidification system comprising a gases flow path configured to generate regions of low and high pressure.

FIG. 11 shows an embodiment comprising a humidification chamber 413 and a main gases flow path 401. The main gases flow path 401 comprises features configured to generate a gases flow 409 from the humidification chamber 413 into the main gases flow 411, 412. The main gases flow path 401 comprises a gases inlet 406, a first portion 402, a second portion 404, and a gases outlet 405. Gases flow into the gases inlet 406 passes through the first and second portions 402, 404 and out the gases outlet 405. The cross sectional area of the first portion 402 is greater than that of the second portion 404.

The gases flow path 411, 412 may comprise a transition portion 403. The transition portion 403 provides for a transition from the first portion 402 to the second portion 404. The inlet aperture 408 is located in the second portion 404 and the outlet aperture 407 is located in the first portion 402. The inlet aperture 408 generates a gases flow 409 from the humidification chamber 413 into the main gases flow path 401. The outlet aperture 408 generates a gases flow 410 from the main gases flow path 401 into the humidification chamber. It is envisaged that the positions of the first portion 402 and second portion 404 could be swapped.

The main gases flow path 1, 101, 201, 301, 401 may be formed in a lid component of a humidification chamber, for example as depicted in FIGS. 3, 6 and 9. The lid component may seal the chamber 13, 113 but for the flow path through the chamber via the outlet aperture 107 and the inlet aperture 108. In the embodiment of FIGS. 7 to 9, the lid component may provide an inlet (not shown) to the chamber separate from the main gases flow path, or the chamber may be provided with an inlet separate from the lid, e.g. via a side wall of the chamber. In some embodiments, the main gases flow path 1, 101, 201, 301, 401 may be provided in a tubular component passing through a gases space of the chamber, for example as depicted in the arrangements of FIGS. 10 and 11, or may be formed in a wall or base of the chamber.

In some embodiments, a connector part may comprise a main gases flow path for connecting a humidification source that is remote from the main gases flow path. FIGS. 12A to 12F illustrate a gases flow connector part 500 comprising a main gases flow path 501. The main gases flow path 501 comprises an inlet portion 502, a neck portion 503, and an outlet portion 504, as described in the earlier embodiments. The embodiment of FIGS. 12A to 12F is similar to the embodiment of FIGS. 7 to 9, in that it has an inlet aperture 508 and is without an outlet aperture. However, in some embodiments an outlet aperture 7, 107, 407 may be provided, to allow a flow of gases from the main gases flow path to enter the humidification source, as described in the embodiments of FIGS. 1 to 3, 4 to 6 and 11. An outlet aperture may be positioned within the inlet portion 502, e.g. near to the inlet end 506 of the main gases flow path 501. The inlet portion 502 is a first portion and the neck portion 503 is a second portion. The first portion 502 comprises a larger cross sectional area than the second portion 503 so that with a flow of gases 511, 512 through the main gases flow path 501 a high pressure region is generated in the first portion 502 and a low pressure region is generated in the second portion 503. With the inlet aperture 508 located near to the second region 503 the low pressure region draws a flow from a humidification source attached to or in communication with the inlet aperture 508. The humidification source, such as a heated humidification chamber may have an inlet (e.g. inlet 26 in FIG. 13) to draw a flow of gases into the humidification source which then pass to the main gases flow path via the inlet aperture 508, as described with reference to the embodiments of FIGS. 7 to 10.

Figure 12A:
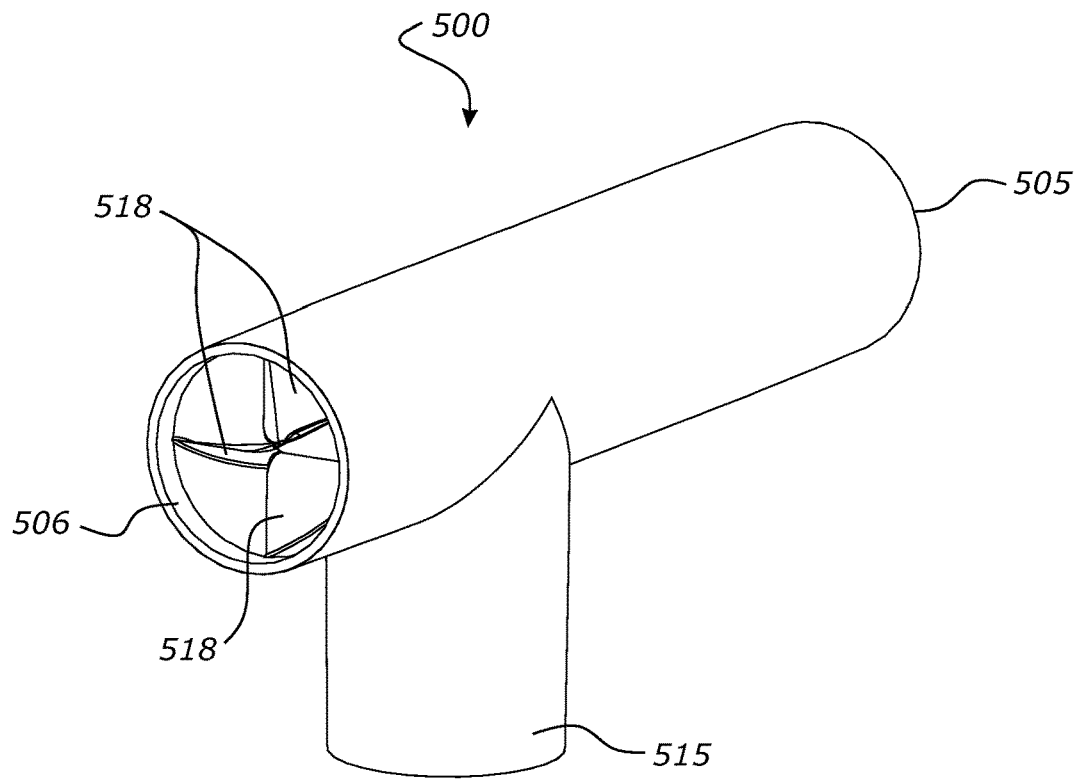
FIG. 12A illustrates a connector comprising a main gases flow path configured to generate regions of low and high pressure.
Figure 12B:
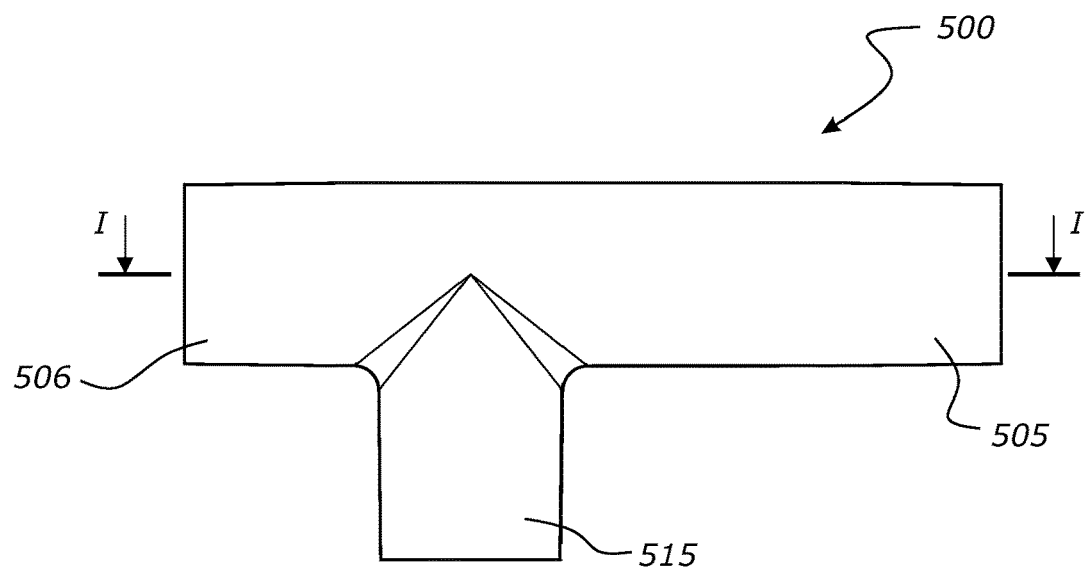
FIG. 12B is a side view of the connector of FIG. 12A.
Figure 12C:
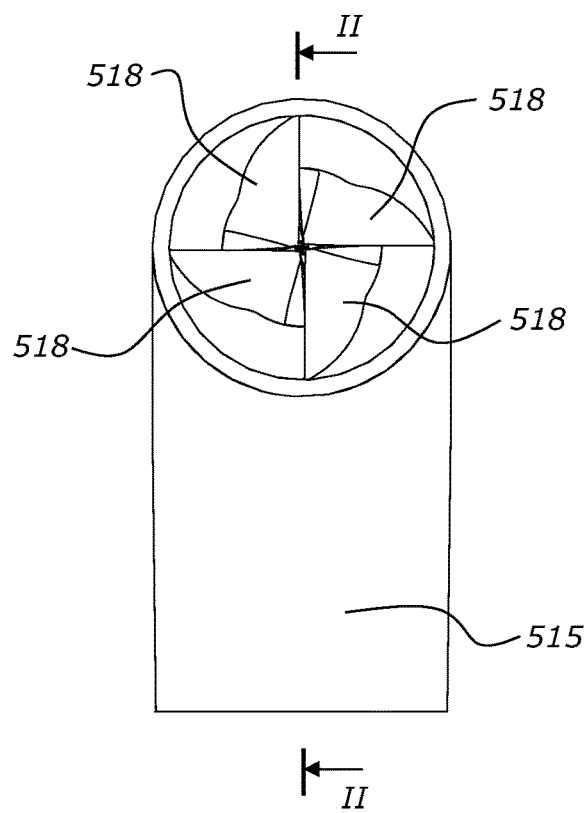
FIG. 12C is an end view on an outlet end of the connector of FIG. 12A.
Figure 12D:
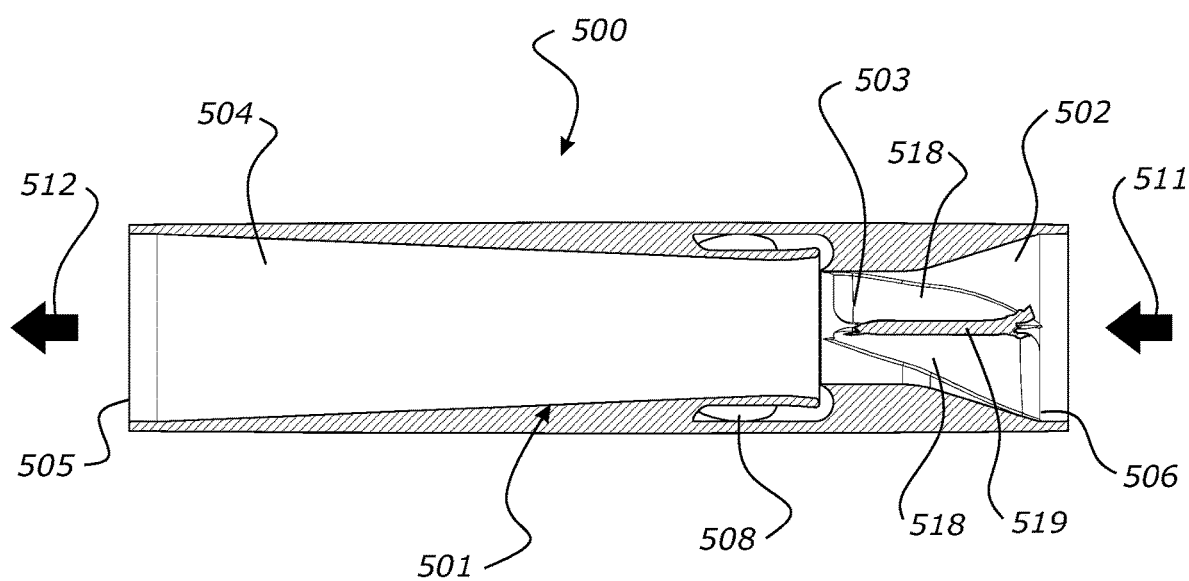
FIG. 12D is a cross sectional view on line I-I in FIG. 12B.
Figure 12E:
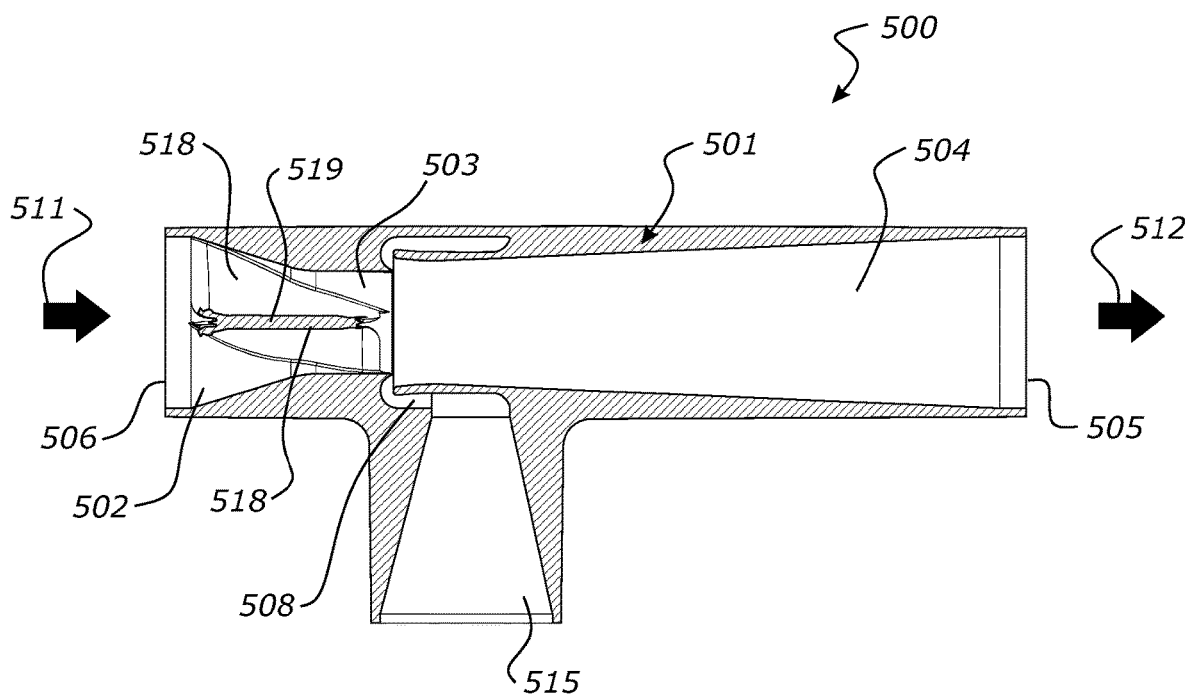
FIG. 12E is a cross sectional view on line II-II in FIG. 12C.
Figure 12F:
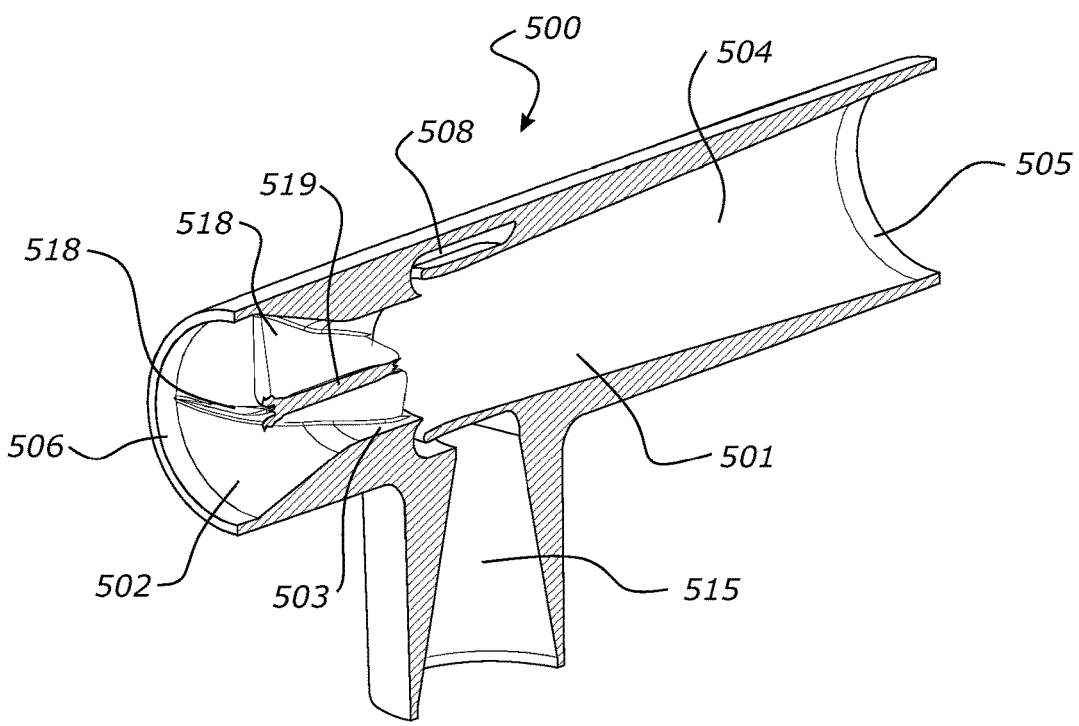
FIG. 12F is a perspective cross sectional view on line II-II in FIG. 12C.

In the embodiment of FIGS. 12A to 12F, the inlet aperture 508 is near to a downstream end of the neck portion 503 (e.g. at or adjacent to the downstream end). In some embodiments, the inlet aperture 508 may be within the neck portion or near to an upstream end of the neck portion. As illustrated in FIGS. 12D and 12F, in some embodiments the inlet aperture 508 may comprise an annular cavity extending at least part way around the main gases flow path. In some embodiments the cavity may extend fully around the main gases flow path. The annular cavity may comprise a toroid cavity with a half cylinder cross section open into the main gases flow path towards an outlet end of the main gases flow path, as shown in FIGS. 12D and 12F. Such an arrangement directs a flow of humidified gases from the humidification source into the main gases flow path in a direction of flow of gases 511, 512 through the main gases flow path from an inlet end to an outlet end of the main gases flow path. This may help to disperse the humidified gases from the humidification source in the gases flow through the main gases flow path, and/or reduce turbulence of flow in the main gases flow path created by mixing of the flow of gases from the humidification source into the main gases flow path.

Figure 13:
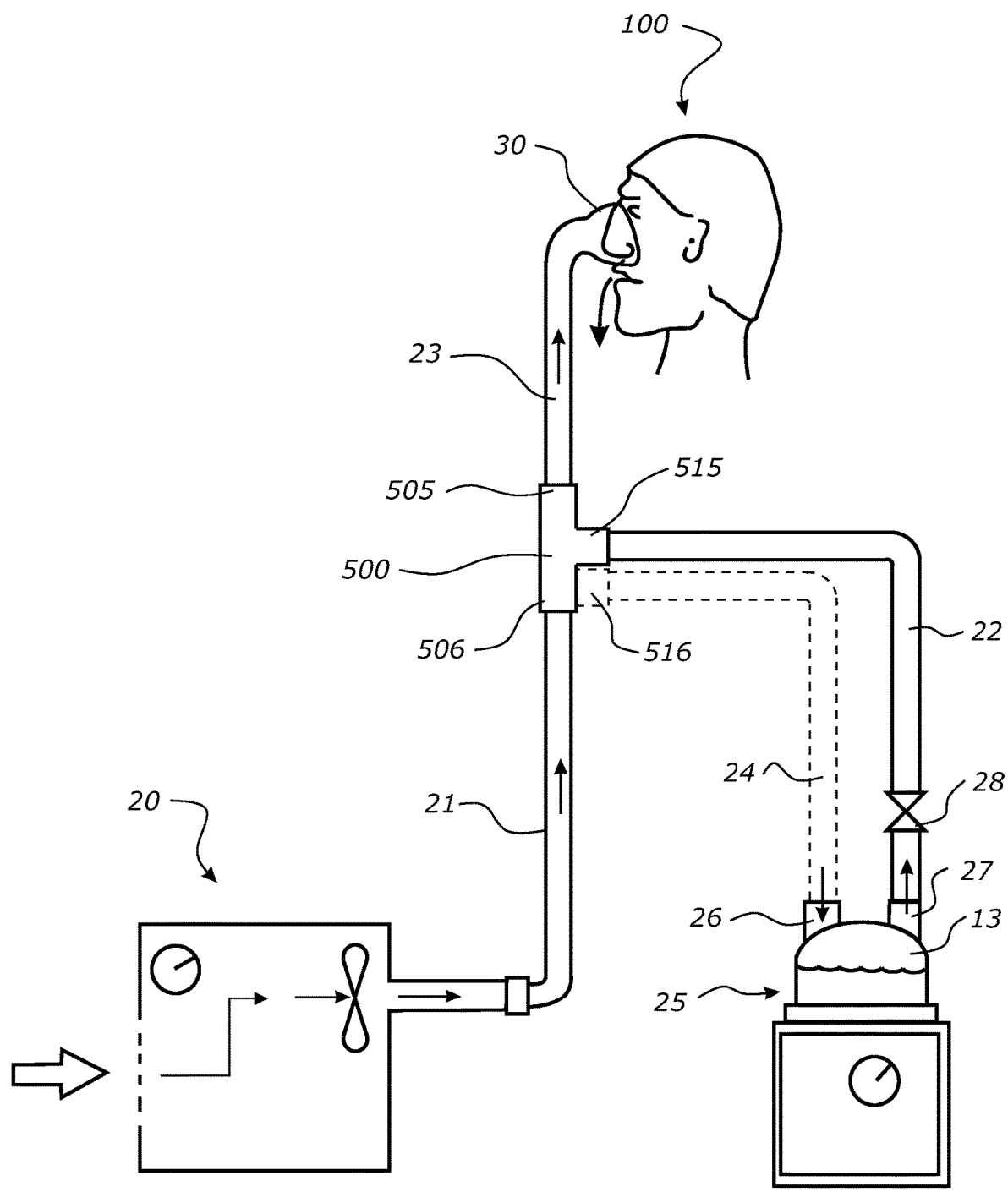
FIG. 13 is a schematic of a humidification system according to at least one embodiment disclosed herein.

The gases flow connector part 500 of FIGS. 12A to 12F comprises a humidification inlet portion 515 for connecting to a humidification source. For example, the humidification inlet portion 515 may form a connector for connecting to a hose or conduit. A humidification source remote from the main gases flow path 501 may be connected to the main gases flow path 501 via a conduit connected to the inlet portion 515. The inlet portion 515 communicates with the main gases flow path 501 via the inlet aperture 508. The gases flow part 500 may be a connector, for connecting a humidification source into a respiratory system providing a flow of respiratory gases from a main gases source to a patient via a patient interface. FIG. 13 illustrates a humidification system comprising a flow source 20 connected to an inlet end 506 of the connector 500 via a conduit 21. A humidification source 25 comprising a humidification chamber 13 is connected to the humidification inlet 515 of the connector 500 via a conduit 22. The humidification source 25 may be remote from the gases flow source 20. In some embodiments, the flow source 20 and the humidification source 25 may be remote from the main gases flow path 501 of the connector 500. The outlet end 505 of the connector 500 is connected to a patient interface 30 to provide a flow of humidified gases to a patient 100. The connector 500 may be near to or directly connected to the patient interface 300, and/or may be connected to the patient interface via a conduit 23. The connector 500 may be a 'T' connector as illustrated, with the inlet portion 515 at a right angle to the main flow path 501. In an alternative embodiment the connector may be a 'Y' connector. In some embodiments the flow source 20 may comprise the main gases flow path 501, or the connector 500 may be near to the flow source 20.

In some embodiments, the system may comprise a valve 28 between the humidification source 25 and the main gases flow path 501. The valve 28 may vary a proportion of humidified gases added to the flow of gases in the main gases flow path 501. For example a user may adjust the valve, or a controller may be provided to control the valve, for example the humidification source may comprise a controller for controlling a flow rate of gases from the humidification source 25 to the main gases flow path 501 by controlling valve 28.

In some embodiments, the connector 500 may comprise an outlet aperture from the main gases flow path and an inlet aperture to the main gases flow path, as described above. In such an embodiment, the connector 500 may comprise a humidification inlet portion 515 and a humidification outlet portion 516 in fluid communication with the inlet aperture and the outlet aperture respectively. A humidification source outlet 27 and a humidification source inlet 26 may be connected to the humidification inlet portion 515 and the humidification outlet portion 516 via respective conduits 22, 24. In FIG. 13 the humidification outlet portion 516 and conduit 24 are illustrated in dashed lines.

Again with reference to FIGS. 12A to 12F, in some embodiments a structure may be provided to cause gases flow 512 in the main gases flow path 501 to swirl (for example swirl about a longitudinal axis of the main gases flow path). The structure causes swirling (e.g. a vortex) of the gases flow in the main gases flow path to help reduce disruption of flow (e.g. turbulence or stalling of flow or disruption of flow boundary layers) caused by mixing of a flow of gases entering the main gases flow path from the humidification source via the inlet aperture 508. The structure may comprise one or more vanes or baffles that interfere with the gases flow to cause the flow to swirl. In the embodiment of FIGS. 12A to 12F the structure comprises four vanes 518. The vanes may extend from a central member 119 to a side wall of the outlet portion 504 and/or the neck portion 503 of the main gases flow path. The structure may be within the inlet portion 502, the neck portion 503 or both. In some less preferred embodiments, the structure may be within the outlet portion 504. Preferably the structure is upstream of the inlet aperture 508. In the illustrated embodiment the vanes 518 extend from near to an inlet end of the inlet portion 502 to near to an outlet end of the necked portion 503. The structure 518 may be provided at or adjacent to the inlet end 506 of the main gases flow path 501. The structure 518 may be provided upstream to the inlet aperture 508. The central member 519 may be coaxial with the main gases flow path. The vane or vanes 518 may be curved to assist with spiraling the gases flow. A single vane may be provided, for example a helical vane with an axis coaxial with the main gases flow.

In the embodiments of FIGS. 1 to 9 and 12A to 12F the main gases flow path may be without one of the inlet portion and the outlet portion. In other words, the neck portion may form an inlet or an outlet portion.

In the above described embodiments, the inlet aperture 8, 108, 208, 308, 408, 508 may be described as an 'injection aperture' or 'injection port', allowing gases from the humidification source to enter the main gases flow path. The outlet aperture 7, 107, 407 may be described as a pressure equalization port, to avoid a vacuum in the humidification source as gases flow from the humidification source to the main gases flow path via the inlet aperture. As described earlier, the outlet aperture 7, 107, 407 and inlet aperture 8, 108, 408, 508 provide a shunt (e.g. parallel) or secondary flow path to divert a portion of the gases flow in the main gases flow path from the main gases flow path through the humidification source and back into the main gases flow path. The flow of gases through the humidification source from the outlet aperture to the inlet aperture is a secondary flow (parallel to or alongside) to the flow of gases along the main gases flow path. As described earlier, in some embodiments, a humidification source inlet (e.g. an equalization port) may be provided separate from the main gases flow path, to allow a flow of gases to enter the humidification source. In an embodiment without an outlet aperture between the main gases flow path and the humidification source, a portion of a flow of gases through the main gases flow path 1, 101, 201, 301, 401, 501 does not enter the humidification source. A flow through the humidification source from the humidifier inlet to the main gases flow via the inlet aperture 8, 108, 408 is a shunt (e.g. parallel) or secondary flow to the flow of gases in the main gases flow path.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include these features, elements and/or states.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

While the above detailed description may have shown, described, and pointed out novel features as applied to various embodiments, it may be understood that various omissions, substitutions, and/or changes in the form and details of any particular embodiment may be made without departing from the spirit of the disclosure. As may be recognized, certain embodiments may be embodied within a form that does not provide all of the features and benefits set forth herein, as some features may be used or practiced separately from others.

Additionally, features described in connection with one embodiment can be incorporated into another of the disclosed embodiments, even if not expressly discussed herein, and embodiments having the combination of features still fall within the scope of the disclosure. For example, features described above in connection with one embodiment can be used with a different embodiment described herein and the combination still fall within the scope of the disclosure.

It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this disclosure may comprise, additional to its essential features described herein, one or more features as described herein from each other embodiment disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added.

Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally,"

and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this description is not, and should not be taken as, an acknowledgement or any form of suggestion that that prior art forms part of the common general knowledge in the field of endeavor in any country in the world.

The invention may also be said broadly to consist in the parts, elements and features referred to or indicated in the description of the application, individually or collectively, in any or all combinations of two or more of said parts, elements or features.

Where, in the foregoing description, reference has been made to integers or components having known equivalents thereof, those integers are herein incorporated as if individually set forth. In addition, where the term "substantially" or any of it's variants have been used as a word of approximation adjacent to a numerical value or range, it is intended to provide sufficient flexibility in the adjacent numerical value or range that encompasses standard manufacturing tolerances and/or rounding to the next significant figure, whichever is greater.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims.

What is claimed is:

1. A humidification system comprising:
   a humidification source configured to humidify gases,
   a main gases flow path comprising a low pressure region, and a high pressure region,
   the main gases flow path comprising an outlet aperture near the high pressure region, the outlet aperture pneumatically connected to the humidification source to allow a secondary gases flow from the main gases flow path into the humidification source,
   the main gases flow path comprising an inlet aperture near the low pressure region, the inlet aperture pneumatically connected to the humidification source to allow the secondary gases flow from the humidification source to return to the main gases flow path; and
   a swirl-inducing structure being positioned to cause a main gases flow to swirl to help reduce disruption of flow caused by mixing of the secondary gases flow from the humidification source through the inlet aperture.

2. The humidification system of claim 1, wherein the humidification source comprises a humidification chamber.

3. The humidification system of claim 1, wherein the high pressure region is greater than a pressure inside the humidification source and/or the pressure inside the humidification source is greater than the low pressure region.

4. The humidification system of claim 1, wherein the outlet aperture is located downstream to the inlet aperture along the main gases flow path.

5. The humidification system of claim 1, wherein the outlet aperture is located upstream to the inlet aperture along the main gases flow path.

6. The humidification system of claim 1, wherein the main gases flow path further comprises a neck portion, an inlet portion and an outlet portion, wherein the neck portion is of a smaller cross-sectional area than the inlet portion and/or the outlet portion.

7. The humidification system of claim 6, wherein the outlet aperture is located near at least one of the inlet portion and/or the outlet portion.

8. The humidification system of claim 6, wherein a cross-sectional area of a part of the neck portion, inlet portion, and/or outlet portion is variable.

9. The humidification system of claim 1, wherein the humidification source is sealed to an external environment.

10. The humidification system of claim 1, wherein the humidification source comprises a valve or an aperture configured to allow gas exchange with an external environment.

11. The humidification system of claim 10, wherein the valve or the aperture is configured to only allow gases from the external environment into the humidification source.

12. The humidification system of claim 1, wherein the secondary gases flow from the humidification source to the main gases flow path is between 0% and 40% of a flow of gases through the main gases flow path.

13. The humidification system of claim 1, wherein the humidification source further comprises a heater configured to heat a humidification chamber.

14. The humidification system of claim 13, wherein the heater is a heater plate.

15. The humidification system of claim 1, wherein a cross-sectional area of a part of the main gases flow path is variable.

16. The humidification system of claim 1, wherein the main gases flow path comprises a valve, the valve configured to vary a flow rate of gases through the main gases flow path.

17. The humidification system of claim 1, wherein the swirl-inducing structure defines a feature configured to change at least one of pressure, velocity, flow rate and a flow profile of the flow of gases through the main gases flow path.

18. The humidification system of claim 17, wherein the feature is at least one of a baffle, diffuser, orifice plate, or texture on a surface of the main gases flow path.

19. The humidification system of claim 17, wherein the feature is actuatable to vary at least one of pressure, velocity, flow rate and a flow profile of the flow of gases through the main gases flow path.

20. The humidification system of claim 1, wherein the swirl-inducing structure causes a main gases flow to swirl about a longitudinal axis of the main gases flow.

21. The humidification system of claim 20, wherein the swirl-inducing structure comprises one or more vanes or baffles.

22. The humidification system of claim 21, wherein the one or more vanes or baffles are curved to interfere with a main gases flow to cause the main gases flow to swirl.

23. The humidification system of claim 21, wherein the swirl-inducing structure comprises four vanes.

24. The humidification system of claim 21, wherein the one or more vanes or baffles extend from a central member to a side wall that at least partially defines the main gases flow path.

25. The humidification system of claim 24, wherein the central member is coaxial with the side wall that at least partially defines the main gases flow path.

26. The humidification system of claim 20, wherein the swirl-inducing structure is positioned upstream of the inlet aperture.

27. The humidification system of claim 20, wherein the swirl-inducing structure is positioned at or adjacent to an inlet portion of the main gases flow path.

\* \* \* \* \*